US008457764B2

(12) United States Patent
Ramachandran et al.

(10) Patent No.: US 8,457,764 B2
(45) Date of Patent: Jun. 4, 2013

(54) EAR IMPLANT ELECTRODE AND METHOD OF MANUFACTURE

(75) Inventors: Anup Ramachandran, Innsbruck (AT); Stefan B. Nielsen, Innsbruck (AT); Claude Jolly, Innsbruck (AT); Martin Zimmerling, Patsch (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 13/173,530

(22) Filed: Jun. 30, 2011

(65) Prior Publication Data
US 2012/0004715 A1    Jan. 5, 2012

Related U.S. Application Data

(60) Provisional application No. 61/359,928, filed on Jun. 30, 2010.

(51) Int. Cl.
*A61N 1/05* (2006.01)

(52) U.S. Cl.
USPC .......................................................... 607/137

(58) Field of Classification Search
USPC ............................ 607/116, 119, 137; 600/379
See application file for complete search history.

(56) References Cited

U.S. PATENT DOCUMENTS

| 5,630,839 | A  | * | 5/1997  | Corbett et al. | 607/137 |
|-----------|----|---|---------|----------------|---------|
| 5,800,500 | A  |   | 9/1998  | Spelman et al. | 607/137 |
| 5,833,714 | A  | * | 11/1998 | Loeb           | 607/56  |
| 6,678,564 | B2 | * | 1/2004  | Ketterl et al. | 607/137 |
| 7,941,228 | B2 | * | 5/2011  | Kuzma et al.   | 607/137 |
| 2005/0234535 | A1 |   | 10/2005 | Risi et al.    | 607/137 |
| 2006/0089700 | A1 | * | 4/2006  | Darley         | 607/137 |
| 2006/0206185 | A1 |   | 9/2006  | Schuller       | 607/137 |
| 2007/0150039 | A1 |   | 6/2007  | Leigh et al.   | 607/152 |
| 2008/0058912 | A1 |   | 3/2008  | O'Brien        | 607/116 |
| 2008/0082141 | A1 |   | 4/2008  | Risi           | 607/57  |

OTHER PUBLICATIONS

ISA/US Commissioner for Patents, International Search Report, PCT/US 11/42555, date of mailing Nov. 14, 2011, 2 pages.

* cited by examiner

*Primary Examiner* — George Evanisko
(74) *Attorney, Agent, or Firm* — Sunstein Kann Murphy & Timbers LLP

(57) ABSTRACT

A novel electrode array is described for ear implant systems such as cochlear implants (CI) and vestibular implants (VI). The electrode array includes electrode wires for carrying electrical stimulation signals. At a terminal end of each electrode wire is an electrode stimulation contact for applying the electrical stimulation signals to adjacent neural tissue. An electrode carrier of resilient material encases the electrode wires and has an outer surface with a plurality of contact openings exposing the stimulation contacts. Multiple bend control elements are distributed along the length of the electrode array to control bending flexibility of the electrode array as a function of a bend radius threshold.

18 Claims, 15 Drawing Sheets

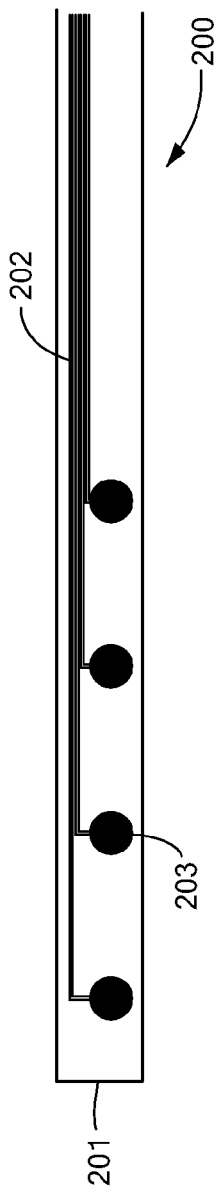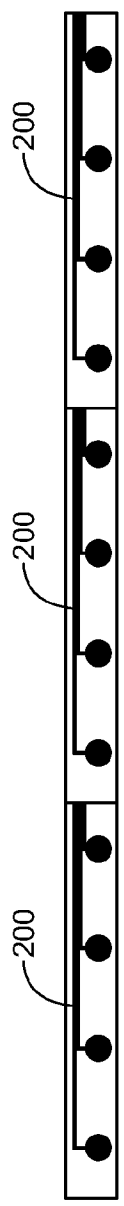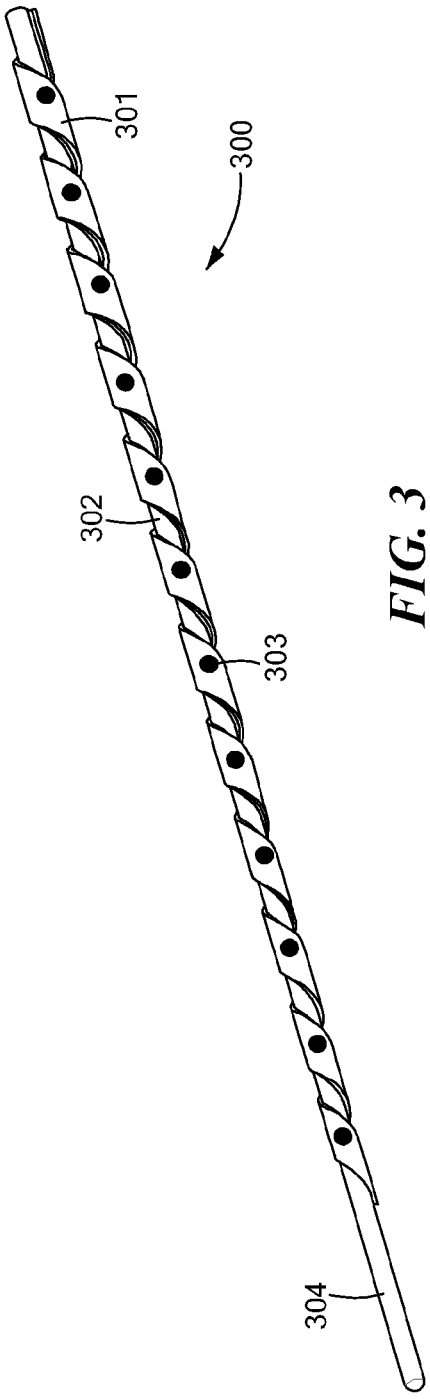

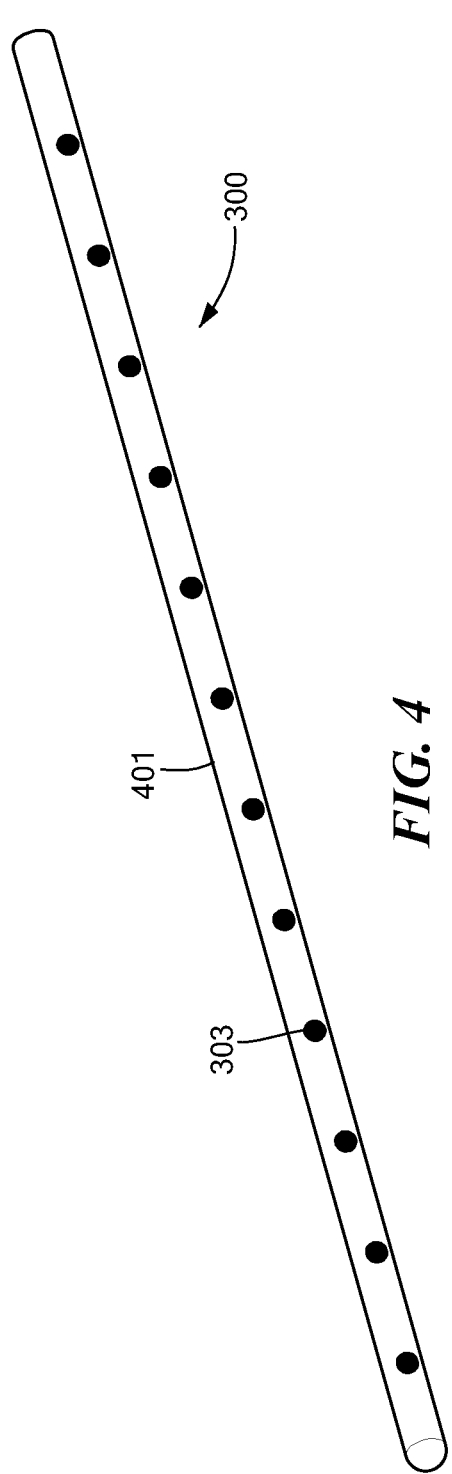
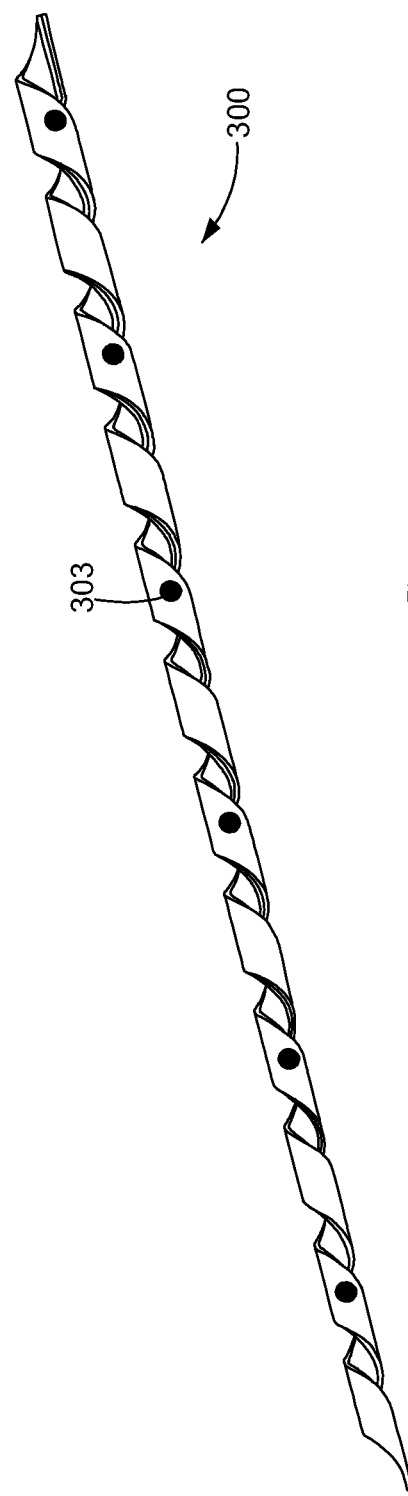
FIG. 4
FIG. 5

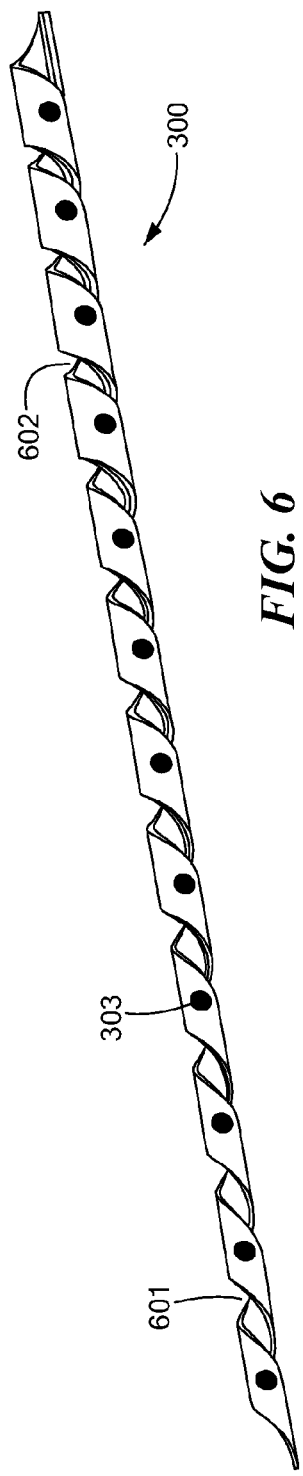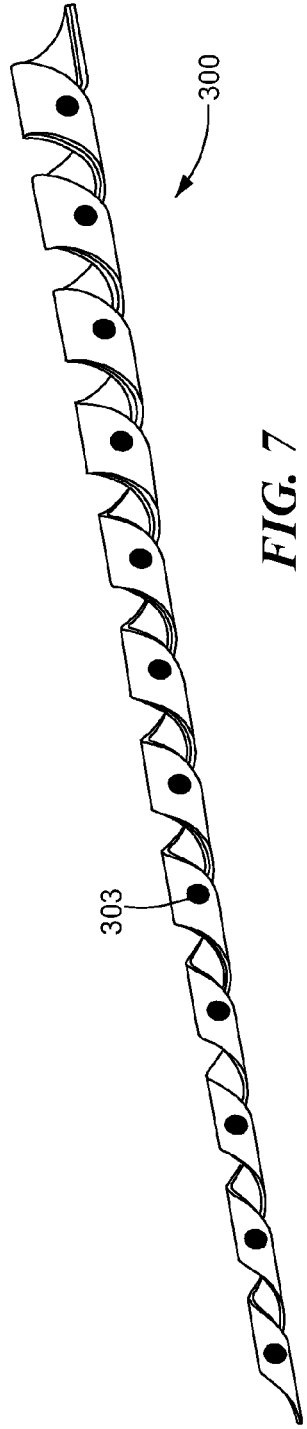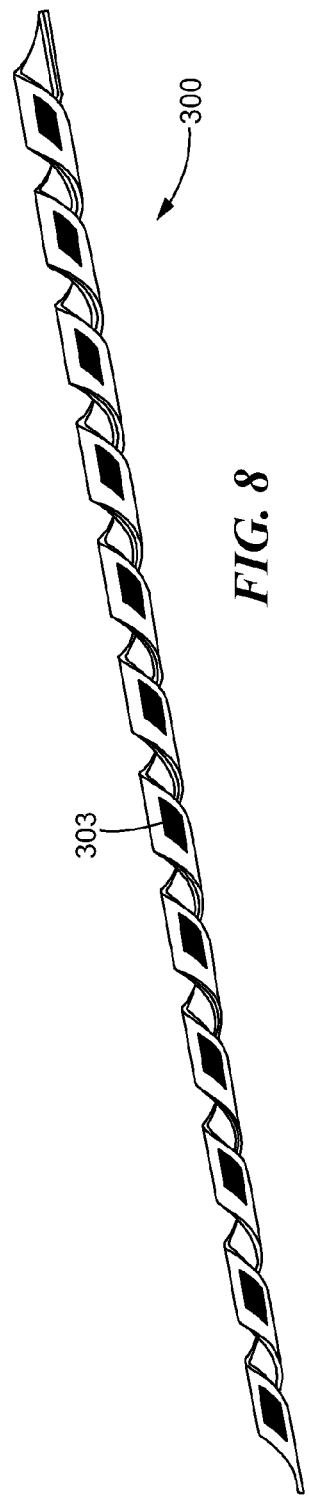

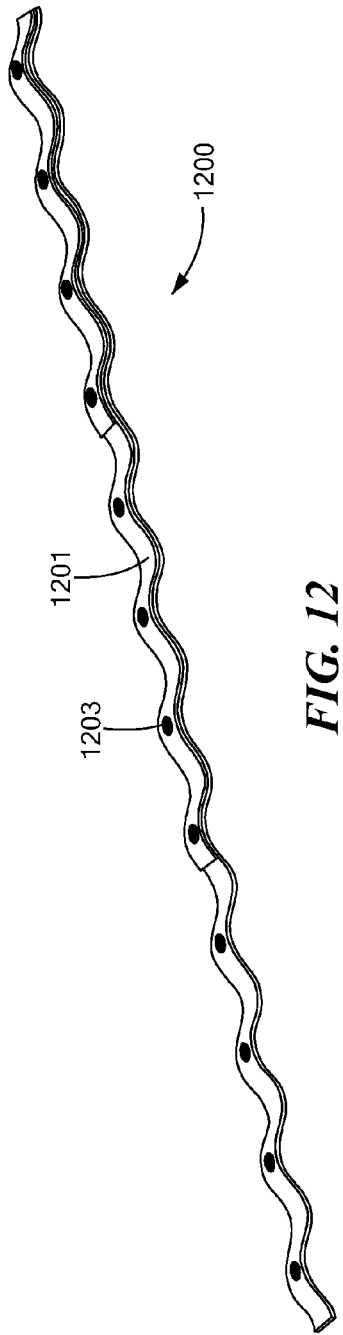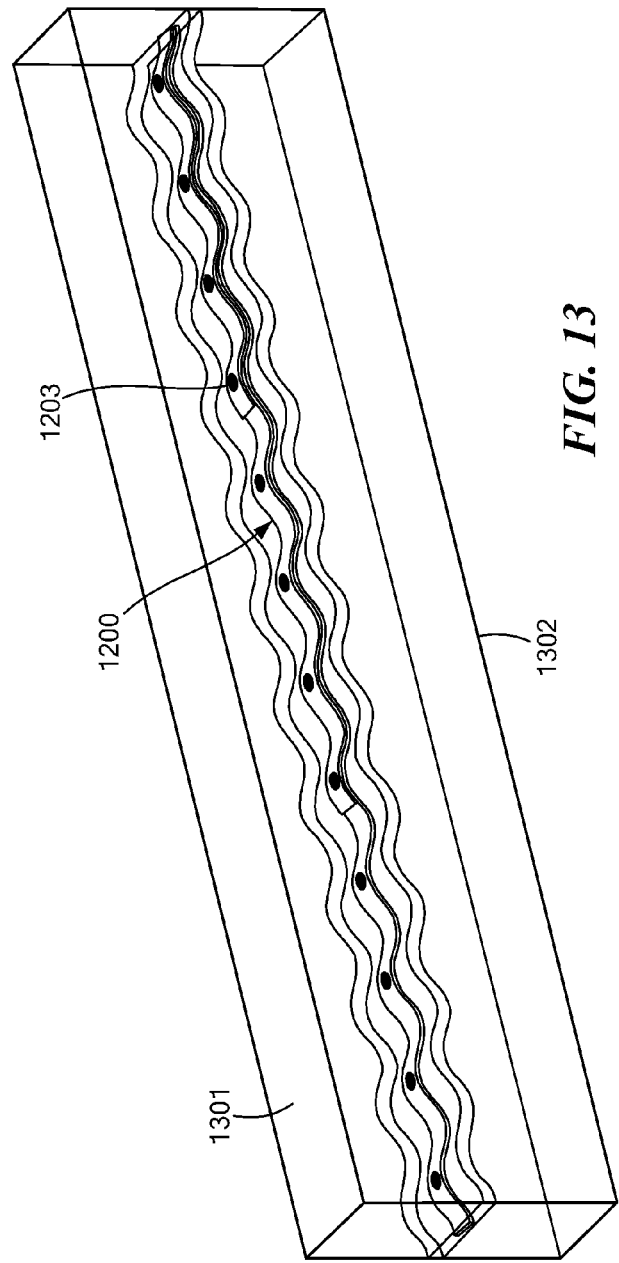
FIG. 12
FIG. 13

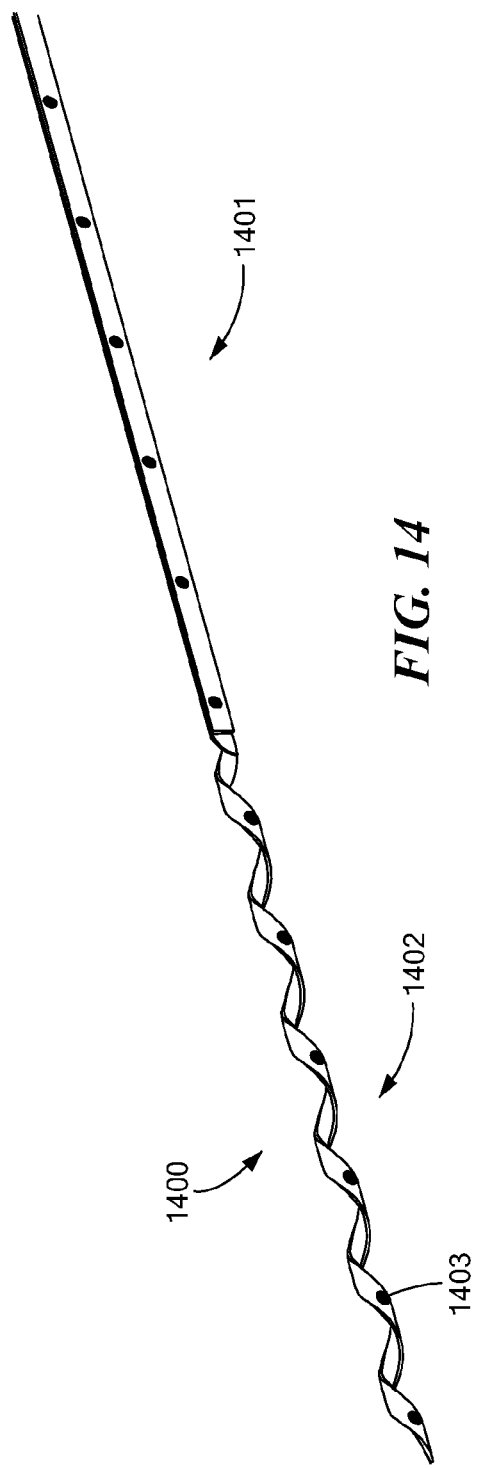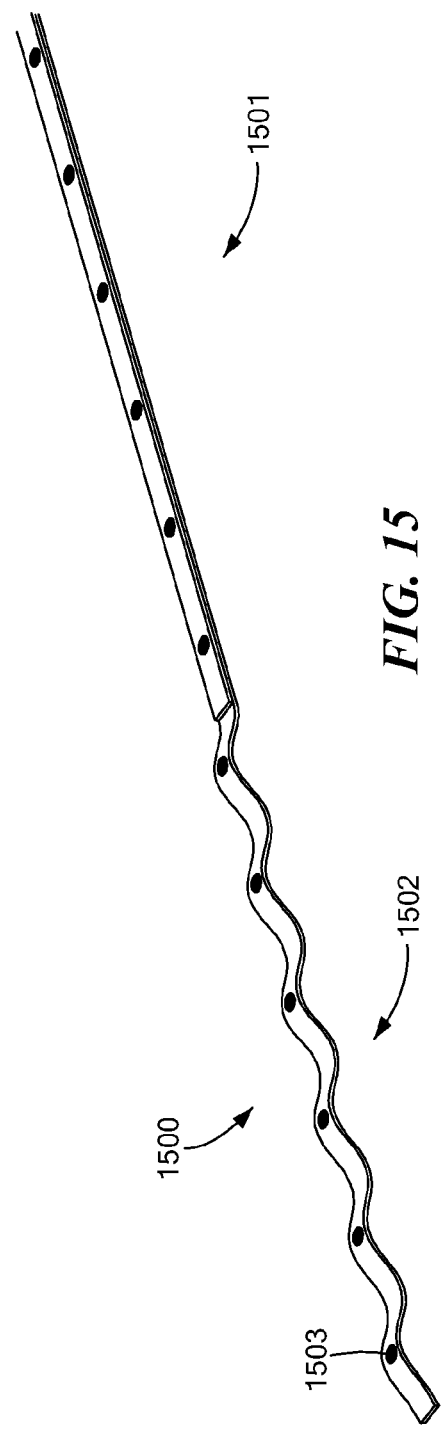

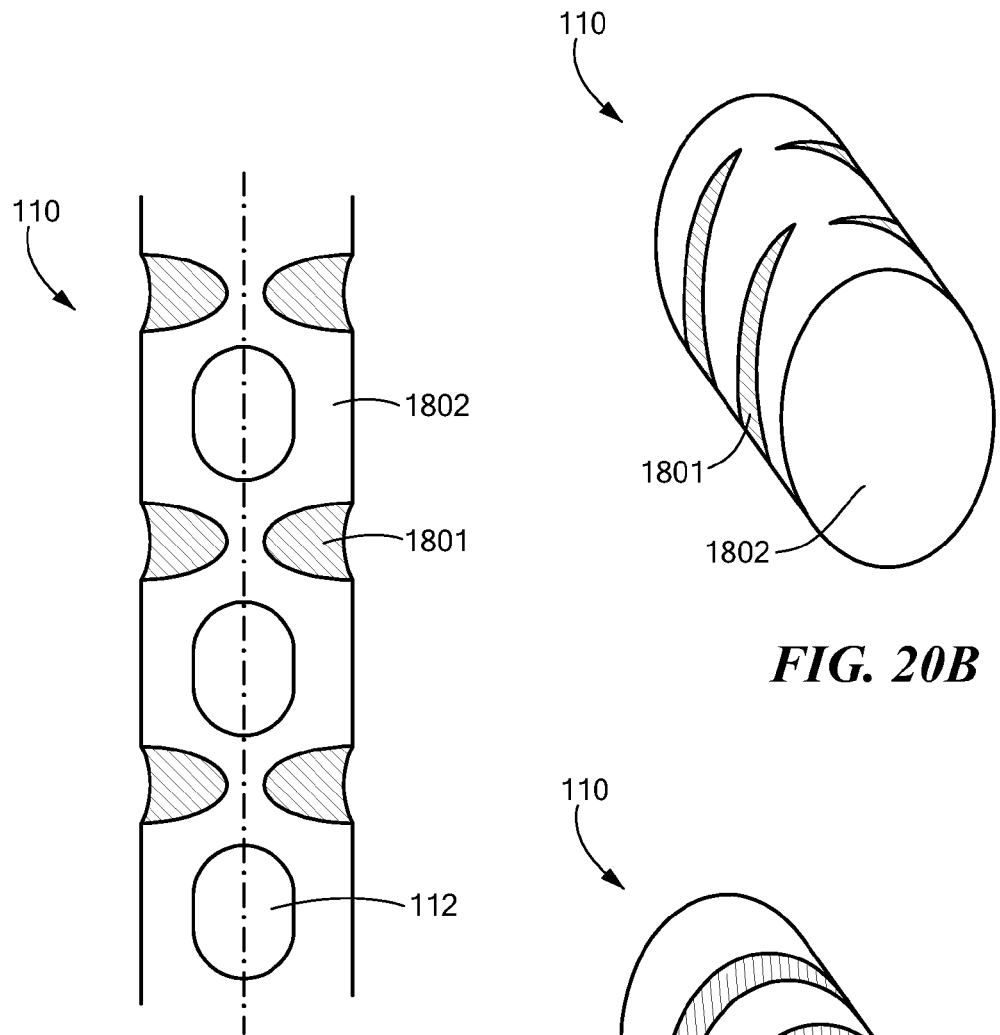
*FIG. 20B*
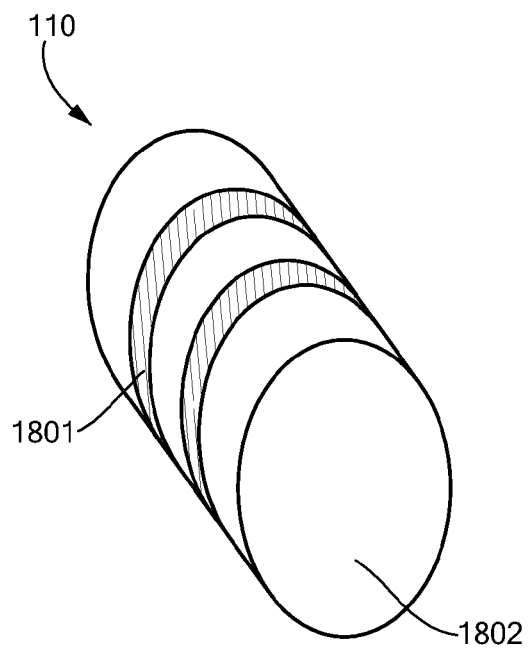
*FIG. 20A*
*FIG. 20C*

EAR IMPLANT ELECTRODE AND METHOD OF MANUFACTURE

This application claims priority from U.S. Provisional Patent Application 61/359,928, filed Jun. 30, 2010, which is incorporated herein by reference.

FIELD OF THE INVENTION

The present invention relates to medical implants, and more specifically to an implant electrode array used in ear implant systems such as cochlear implants (CI) and vestibular implants (VI).

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode contact can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple stimulation contacts 112 on its surface that provide selective stimulation of the cochlea 104.

The electrode array 110 contains multiple electrode wires embedded in a soft silicone body referred to as the electrode carrier. The electrode array 110 needs to be mechanically robust, and yet flexible and of small size to be inserted into the cochlea 104. The material of the electrode array 110 needs to be soft and flexible in order to minimize trauma to neural structures of the cochlea 104. But an electrode array 110 that is too floppy tends to buckle too easily so that the electrode array 110 cannot be inserted into the cochlea 104 up to the desired insertion depth.

Typically, the electrode wires within the electrode array 110 have a homogenous overall shape from one end to the other: either generally straight, repeating coiled loops, or recurring wave shapes. As shown in FIG. 17, the bend radius of the electrode array 110 becomes ever smaller as it is inserted more deeply into the cochlea. So the electrode array 110 should have non-uniform and non-homogeneous mechanical properties (e.g., bending and flexing) to accommodate the complex path that it must take, and also for maintaining biological compatibility with the surrounding tissue of the cochlea 104.

In addition, present cochlear implant (CI) systems possess numerous stimulation contacts 112 along the electrode array 110 for achieving a frequency distribution and resolution that mimics natural human hearing as far as possible. As the technology advances it is likely that an increasing number of frequency bands will need to be supported by the CI systems for providing an even finer pitched hearing. Consequently, more and more wires and stimulation contacts 112 will have to be placed within the electrode array 110, whose dimensions are restricted by the very limited space in the cochlea 104. In general, it can be said that the more channels (i.e. wires and contacts) an electrode array 110 contains, the more rigid it will be due to the higher amount of metal structures within it.

A trade-off needs to be made between a certain stiffness of the electrode array 110 which allows insertion into the cochlea 104 up to the desired insertion depth without the array buckling, and certain flexibility of the electrode array 110 which keeps mechanical forces on the lateral wall of the scala tympani of the cochlea 104 low enough.

Recent developments in CI electrode array designs and surgical techniques are moving towards minimal trauma implantations. For preservation of residual hearing it is of particular importance to preserve the natural intra-cochlear structures. Therefore, the size and mechanical characteristics of the electrode array are critical parameters for the best patient benefit. Some electrode array designs are pre-curved, though a drawback of that approach is that a special electrode insertion tool is needed which keeps the electrode array straight until the point of insertion.

As documented by Erixon et al., *Variational Anatomy of the Human Cochlea: Implications for Cochlear Implantation*, Otology & Neurotology, 2008 (incorporated herein by reference), the size, shape, and curvature of the cochlea varies greatly between individuals, meaning that a CI electrode array must match a wide range of scala tympani (ST) geometries. Furthermore, recently published research by Verbist et al., *Anatomic Considerations of Cochlear Morphology and Its Implications for Insertion Trauma in Cochlear Implant Surgery*, Otology & Neurotology, 2009 (incorporated herein by reference) has shown that the human ST does not incline towards the helicotrema at a constant rate, but rather there are several sections along the ST where the slope changes, sometimes even becoming negative (i.e. downwards). The location and grade of these changes in inclination were also found to be different from individual to individual. Consequently, CI electrode arrays should be highly flexible in all directions in order to adapt to individual variations in curvature and changes in inclination of the ST for minimal trauma implantation.

Present day CI electrode arrays require considerable amount of hand assembly during manufacturing. Single thin platinum wires covered with a thin electrical insulation must be cut to size and manipulated without compromising the insulation. The wires must be stripped of insulation at the ends and welded to small thin platinum foils that act as stimulation contacts. Each wire must be individually placed inside a mold and assembled in a multi-channel structure before being silicone injection molded. Demolding of long electrodes must take place without causing damage to the structure.

Some rejects inevitably occur during manufacturing due to open or short circuits between wires, or poor welding to the contacts. Silicone overflow on contact surfaces may cause further rejects. The process of making electrodes is extremely labor intensive and a considerable percentage of rejected electrodes is unavoidable since maintenance of acceptable quality is difficult. In addition, the manual work is very operator dependent and difficult to specify in adequate detail to give reproducible results. Hand-made devices may therefore unintentionally and undesirably be subject to significant variations in performance. Furthermore, manual work is linked with extensive and time-consuming training of personnel and manual production may in general not be financially competitive.

It would therefore be desirable to have a streamlined method for making implant electrodes using an automated process. The requirements as to number of stimulation channels, size, and mechanical properties constitute a challenging problem for traditional and modern electrode manufacturing techniques. U.S. Pat. No. 6,374,143 by Berrang et al. ("Berrang", incorporated herein by reference) presents a process for fabricating thin-film CI electrodes by encapsulating platinum structures between two polymer films. This process can be automated and thus attempts to address the problem of a lacking streamlined electrode manufacturing as described above. In the same patent, folding is suggested for miniaturization of an electrode array in order to pack the many metal wires into a smallest possible space. U.S. Pat. No. 7,085,605 by Bluger et al. ("Bluger", incorporated herein by reference) discloses a similar method for an implantable medical assembly. WO2008/011721 by Spruit ("Spruit", incorporated herein by reference) proposes stacking of several individual assembly layers for essentially achieving the same compact structure. Other methods for manufacturing a thin-film CI electrode include ink-jet printing of platinum ink onto a polymer film, as suggested by U.S. patent application Ser. No. 12/787,866, filed May 26, 2010 (incorporated herein by reference).

As the number of stimulation channels increases, an increasing number of folded or stacked layers is needed for electrically insulating the conducting metal wires from each other. One basic mechanical property of the described (folded or stacked) assemblies is the highly inhomogeneous bending characteristics in different directions, mainly caused by the geometry of the assembly layers containing the wires. The cross-section of these layers is rectangular in shape and therefore has a preferred bending direction. Existing and suggested CI electrode arrays based on the thin-film technology were therefore designed to be highly bendable in the direction of the ST curvature around the modiolus, but far less flexible in the plane parallel to the modiolus. As explained earlier, these characteristics are generally not desirable in CIs since they should be highly bendable in all directions to lower the risk of implantation trauma.

U.S. Pat. No. 5,964,702 ("Grill", incorporated herein by reference) describes stimulating peripheral nerves using cuff electrodes wound in a helical shape where the stimulation contact surfaces are opened inwards towards the internal lumen of the helical shape. WO93/20887 ("Grill WO", incorporated herein by reference) describes a similar arrangement for thin film implant electrodes. Both Grill methods use a first layer of elastomer that is cured and stretched and then covered by second layer of elastomer so that the different mechanical tensions in the two elastomer layers cause the layered structure to curl into a helix. But in pacemaker electrodes, the size constraints, the number of electrically active channels, and the requirements to flexibility (for preservation of delicate tissues) are fundamentally different than for many specific implant applications such as CI electrodes. It is therefore a challenge to produce CI electrodes that make use of the highly flexible helical shaped wires.

U.S. Patent Publication 2010/0305676 ("Dadd," incorporated herein by reference) describes winding the electrode wires in the extra-cochlear segment of the electrode lead in a helical shape to make that portion of the electrode lead stronger. Dadd is quite clear that such a helical portion does not extend into the intra-cochlear electrode array which needs to be much more flexible than the extra-cochlear lead in order to minimize trauma to the cochlear tissues when the array is inserted.

U.S. Patent Publication 2010/0204768 ("Jolly," incorporated herein by reference) describes winding the individual electrode wires in the intra-cochlear electrode array in an elongated helical shape where each wire is separate and independent.

SUMMARY OF THE INVENTION

Embodiments of the present invention are directed to an electrode array for ear implant systems such as cochlear implants (CI) and vestibular implants (VI). At a terminal end of each electrode wire is an electrode stimulation contact for applying the electrical stimulation signals to adjacent neural tissue. An electrode carrier of resilient material encases the electrode wires and has an outer surface with a plurality of contact openings exposing the stimulation contacts. Multiple bend control elements are distributed along the length of the electrode array to control bending flexibility of the electrode array as a function of a bend radius threshold. The bend control elements may be made of a softer material than the electrode carrier material. The bending flexibility may be controlled to be greater for bending less than the bend radius threshold and lesser for bending greater than the bend radius threshold. The bending flexibility may be anisotropic to be greater in one direction than another.

In further specific embodiments, there may be an electrode array core encased within the electrode carrier made of a flexible polymer material within which are embedded the electrode wires. The array core includes an elongated helical portion having multiple helical turns, in which case, the bend control elements may be formed by sections of the electrode carrier between helical turns of the array core.

In such an embodiment, every helical turn may have a stimulation contact. Or not every helical turn may have a stimulation contact, for example, every second helical turn may have a stimulation contact. The array core may have a constant or variable distance between helical turns. The helical shape may have a substantially constant diameter, or a diameter that decreases towards one end. The helical portion of the array core may include substantially all of the electrode array. Or there may be a second portion of the array core having a substantially planar shape or an elongated wavy shape having a plurality of recurring waves. The elongated helical portion may contain a pattern of smaller recurring waves.

In specific embodiments, each stimulation contact may be split into multiple contact sections electrically connected by corresponding connecting sections. The stimulation contacts may be formed on contact wings perpendicular to the electrode wires, which in turn may be supported by the array core.

BRIEF DESCRIPTION OF THE DRAWINGS

FIG. 2A shows an example of a typical thin-film array core subassembly.

FIG. 2B shows an example of a complete thin-film array core assembly containing multiple subassemblies.

FIG. 3 shows an example of a thin film array core having a helical shape according to an embodiment of the present invention.

FIG. 4 shows an example of helical shaped array core over-molded with a resilient electrode carrier material to form a whole electrode array.

FIG. 5 shows an example of helical shaped array core having a stimulation contact on every other helical turn.

FIG. 6 shows an example of helical shaped array core wherein the spacing between helical turns decreases from one end to the other.

FIG. 7 shows an example of helical shaped array core wherein the helix diameter decreases from one end to the other.

FIG. 8 shows an example of helical shaped array core wherein the stimulation contacts have a trapezoid shape.

FIG. 12 shows an example of a thin film array core having a wavy shape according to an embodiment of the present invention.

FIG. 13 shows an example of molding arrangement for manufacturing a wavy shape thin film array core according to an embodiment of the present invention.

FIG. 14 shows an example of a thin film array core having a helical wound portion and a planar portion.

FIG. 15 shows an example of a thin film array core having a wavy shape portion and a planar portion.

FIG. 20 A-C shows another embodiment of an electrode array having bend control elements according to an embodiment of the present invention.

DETAILED DESCRIPTION OF SPECIFIC EMBODIMENTS

Embodiments of the present invention are directed to an ear implant electrode array. Bend control elements are distributed along the length of the electrode array to control bending flexibility of the electrode array as a function of a bend radius threshold. For a bending radius below the threshold which an electrode array normally can reach within the cochlea due to cochlear anatomy, the flexibility of the electrode array is maximum (i.e. minimum spring-back force when bent), But for a bending radius below the threshold, (less than the smallest radius of the outer wall inside the scala tympani), the electrode array has an increased spring-back force. The highly flexible behavior for bending radiuses above the threshold allows electrode array insertion with reduced insertion forces and insertion trauma on the lateral wall of the cochlea. The increased spring-back behavior for bending radiuses below the threshold allows electrode array insertion without kinking or buckling.

Figure 18B:
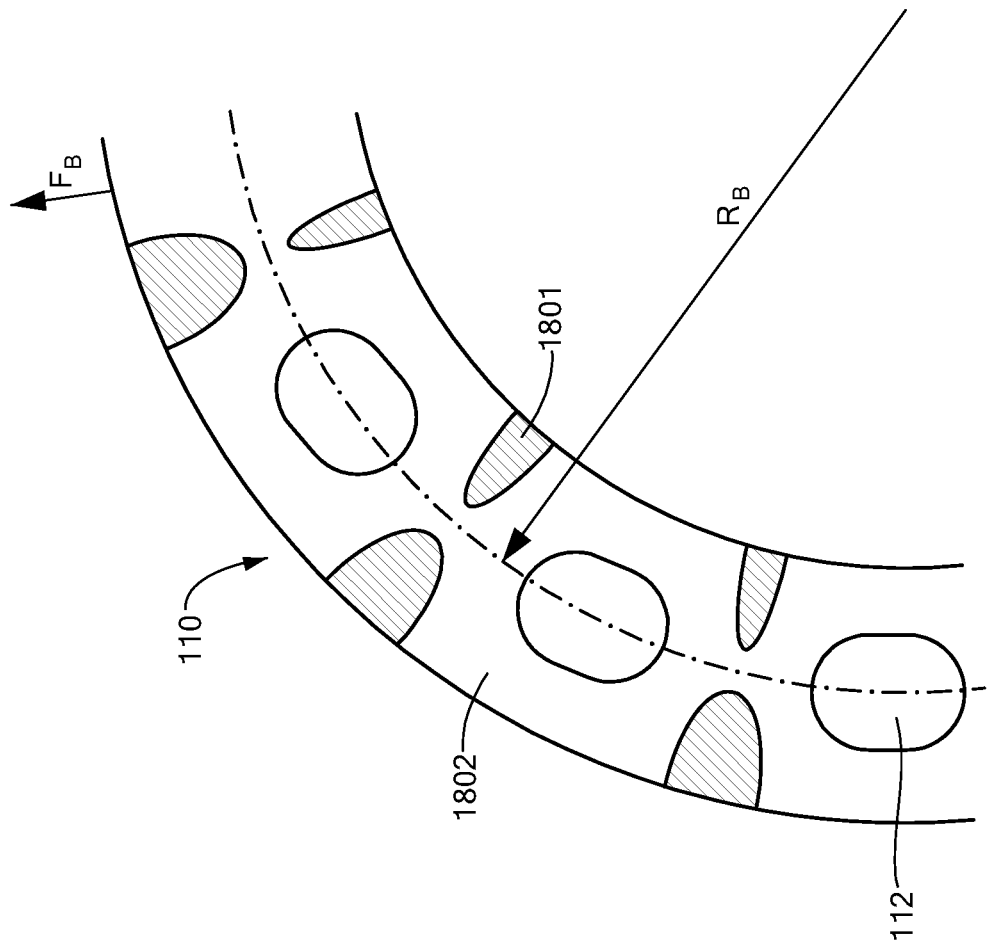
FIG. 18 A-B shows an example of an electrode array containing bend control elements according to an embodiment of the present invention.
Figure 18A:
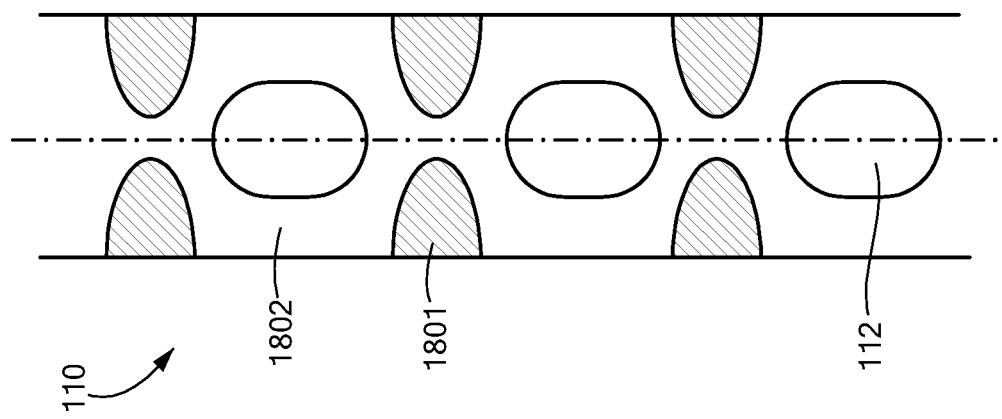

FIG. 18 A-B shows an example of an electrode array 110 containing bend control elements according to an embodiment of the present invention. At a terminal end of each electrode wire within the electrode array 110 is an electrode stimulation contact 112 for applying the electrical stimulation signals to adjacent neural tissue. An electrode carrier 1802 of resilient material encases the electrode wires and has an outer surface with a plurality of contact openings exposing the stimulation contacts 112. Multiple bend control elements 1801 are distributed along the length of the electrode array 110 to control bending flexibility of the electrode array 110 as a function of a bend radius threshold.

The bend control elements 1801 may be made of a softer material than the material of the electrode carrier 1802. Bending flexibility may be controlled to be greater for bending less than the bend radius threshold and lesser for bending greater than the bend radius threshold. The geometry and arrangement of the bend control elements 1801 can be optimized such that the electrode array 110 can easily bend down to a minimum radius which can occur during insertion into the cochlea 104. For example, the bend radius threshold may typically be greater than half of the inner diameter of the scala tympani of the cochlea 104.

Though isotropic bending flexibility may be workable, anisotropic flexibility (i.e. a preferred bending direction of the electrode array) may also help to minimize trauma to the outer wall of the cochlea 104. For example, the bend control elements 1801 on the inner curve of the bend may be implemented so as to easily compress, while the bend control elements 1801 on the outer curve of the bend may be implemented so as to easily elongate.

The geometry and arrangement of the bend control elements 1801 in the electrode array 110 may vary from the apical end to the basal region of the electrode array 110 Thus there may be a smaller bend radius threshold in the apical region (tip region) of the electrode array 110 while the bend radius threshold may be larger in the basal region of the electrode array 110.

Figure 19A:
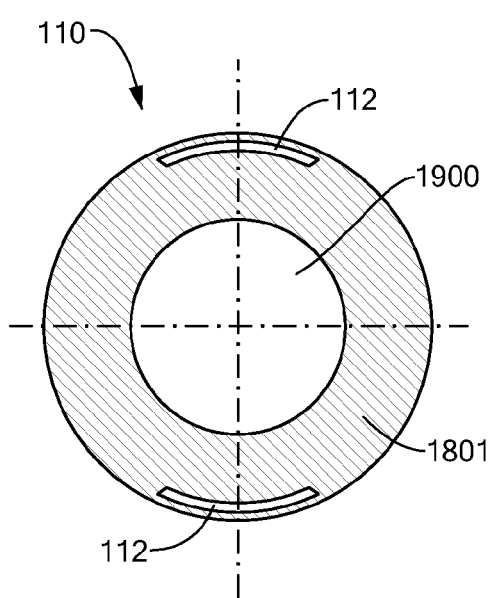
FIG. 19 A-C shows cross-sectional views of different shaped electrode array bend control elements.
Figure 19B:
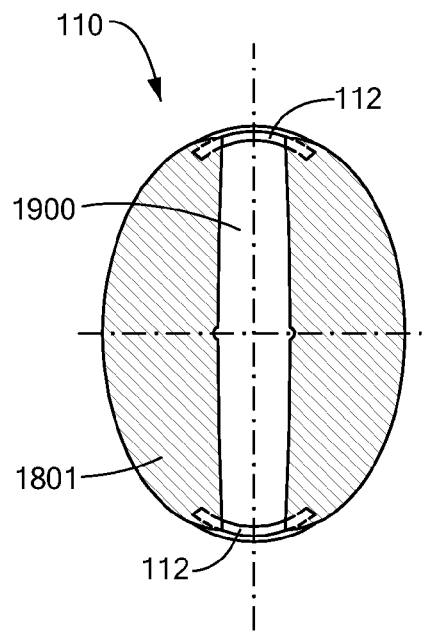
Figure 19C:
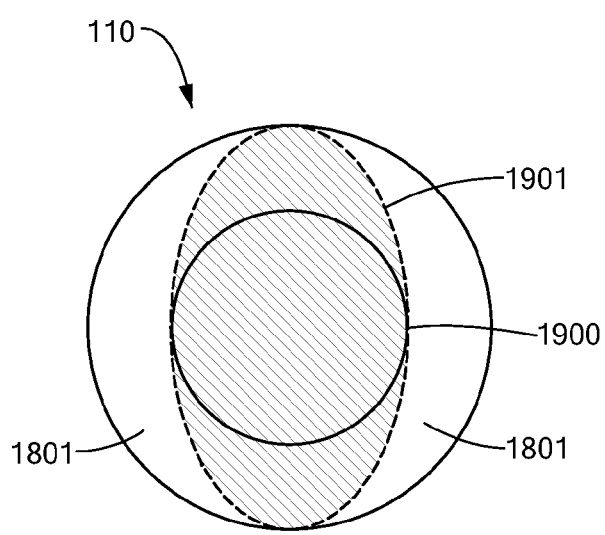

FIG. 19 A-C shows cross-sectional views of different shaped electrode array bend control elements 1801 such as those from FIG. 18. In the circular electrode array 110 embodiment shown in FIG. 19A, the bend control elements form an outer ring encasing the material of the array core 1900, which may be for example, an elongated helical shaped core. The inner circular region inside the array core 1900 could be an empty channel (for example, for delivering therapeutic drugs) or it could be filled with silicone carrier material. For example, the material within the helically shaped array core 1900 may be a harder form of silicone material while the bend control elements 1801 outside the array core 1900 may be formed of a softer type silicone. In the oval shaped electrode array 110 embodiment shown in FIG. 19B, the bend control elements 1801 form oval side sections on either side of the array core 1900. FIG. 19C shows a cross section of an electrode array 110 having a helically shaped array core 1900 with a region of harder carrier material 1901 extending out beyond the outer surface of the array core 1900 (darkened the oval cross section) while on the sides of the electrode array 110 there is softer silicone material as the bend control elements 1801. Such an embodiment highlights the anisotropy bending/flexibility property of the electrode array 110, i.e. different bending properties in the x/y-plane and the z-plane.

FIG. 20 A-C shows another embodiment of another embodiment of an electrode array 110 having bend control elements 1801 that are recessed lower than the outer surface of the electrode carrier 1802. As shown in FIG. 20B, the bend control elements 1801 may form crescent shapes that extend partially around the circumference of the electrode array 110. Or as shown in FIG. 20C, the bend control elements 1801 may form a ring completely around the outer circumference of the electrode array 110.

The bend control elements 1801 may be made of material with a shore hardness (i.e. durometer, type A; e.g., silicone with shore hardness of 10-30) which is less than the shore hardness of the electrode carrier material (typically silicone with a shore hardness of around 40). Alternatively bend control functionality could be implemented by using one or more shaping wires embedded into the electrode carrier.

An embodiment could have bend control elements 1801 on the inner side of the electrode carrier 110 may be made of a different material different from that of the bend control elements 1801 on the outer side of the electrode array 110. For example the inner side bend control elements 1801 could absorb only a small amount of water while those bend control elements 1801 located on the outer side of the electrode array 110 may absorb more water (thus increasing in volume). Such an electrode array 110 would automatically bend upon insertion into the cochlea 104.

In some embodiment the bend control elements 1801 may include drugs and/or lubricants. Or the extra-soft elements may have reduced friction than electrode carrier material. Where the bend control elements 1801 have a higher friction than the electrode carrier material, they may have a slightly smaller diameter than the main silicone elements of the electrode array 110.

Specific examples of silicone materials with medium shore hardness include silicone elastomer MED4244 from NuSil Technology, while silicone elastomer MED4211 from NuSil Technology could be useable as an extra-soft material:

| Property | units | MED 4244 | MED 4211 |
| --- | --- | --- | --- |
| shore hardness (durometer, type A) | | 40 | 25 |
| Elongation | % | 300 | 530 |
| Tensile strength | psi (MPa) | 850 (5.9) | 675 (4.7) |

Similarly, silicones from Applied Silicone also could be workable, with a silicone with medium shore hardness being Liquid Silicone Rubber LSR40, and as extra-soft silicone, e.g. LSR25:

| Property | units | Applied LSR 40 | Applied LSR 25 |
| --- | --- | --- | --- |
| shore hardness (durometer, type A) | | 40 | 25 |
| Elongation | % | 350 | 400 |
| Tensile strength | psi | 800 | 700 |

Embodiments of the present invention also are directed to a new electrode array design and a method of manufacturing such an electrode array to overcome some of the disadvantages of previous thin-film electrode arrays. Improved flexibility in a planar thin film electrode array can be realized based on several specific array core shapes such as a helical shape and a wavy shape array core. Such shapes improve the flexibility of the planar electrode circuit, which in turn helps preserving tissue when the electrode array is surgically implanted, for example, preserving the cochlear tissue in the cochlea.

The Jolly electrode array described in U.S. Patent Publication 2010/0204768 describes winding the individual wires in the electrode array in a helical shape where each wire is separate and independent. However, the Jolly arrangement is not suitable for use with the thin-film electrode array where the wires are embedded together in a common polymer material that must be manipulated as a single structure. Nor is it easy to simply wind a thin-film electrode array into a helical shape.

As the number of stimulation channels increases, a thin-film electrode array needs an increasing number of folded or stacked layers for electrically insulating the conducting metal wires from each other. One basic mechanical property of the described (folded or stacked) assemblies is the highly non-homogeneous bending characteristics in different directions, mainly caused by the geometry of the assembly layers containing the wires. The cross-section of these layers is rectangular in shape and therefore has a preferred bending direction. Existing and suggested CI electrode arrays based on the thin-film technology were therefore designed to be highly bendable in the direction of the ST curvature around the modiolus, but far less flexible in the plane parallel to the modiolus. As explained earlier, these characteristics are generally not desirable in CIs since they should be highly bendable in all directions to lower the risk of implantation trauma.

Moreover, the conventional approach to forming a thin-film electrode array is to stack the sub-assembly layers, and then heat them to melt the polymer film material into a single structure. But when shaping a planar multi-layered thin-film electrode wiring structure into a helix there will be significant forces acting on the inner and outer layers, especially as the stack grows thicker. This potentially could damage the wiring structures in these layers. That makes such structures unsuitable for use as ear implant electrode arrays.

But embodiments of the present invention are able to overcome these problems. If the stacked sub-assembly layers are wound into a helical shape before bonding the layers together, and then heat treat them to melt the layers together and simultaneously set the helical shape. This change in the production process will leave each of the sub-assembly modules in a comparably stress-free condition that is now workable for use as an intra-cochlear electrode array. This same approach also would for work for other shapes such as wavy shaped structures, etc.

FIG. 2A shows an example of a typical thin-film array core subassembly 200 suitable for specific embodiments of the present invention where a thin film array core 201 encloses the electrode wires 202 while having openings on the outer surface that expose the stimulation contacts 203. FIG. 2B shows an example of a complete thin-film array core assembly 204 containing multiple subassemblies 200. In a complete array core assembly 204, the electrode wires carry the electrical stimulation signals from an implant housing at the base end (the electrode lead) to the stimulation contacts 203 which apply the electrical stimulation signals to target neural tissue. Array core subassemblies 200 and array core assemblies 204 may be produced, for example, as described by Berrang or Jolly and stacked or folded as already described by Spruit and Bluger. The number of array core assemblies 200 used in the complete array core assembly 204 depends on the specific array core design. Size of the stimulation contacts 203 and electrode wires 202 and the number of stimulation channels are primary parameters that determine the number of core sub-assemblies 204 that are needed, but also process limitations such as the placement accuracy of the electrode wires 202 and stimulation contacts 203 with respect to the thin film array core 201 also may play a role.

FIG. 3 shows an example of a thin film array core 300 having a helical shape according to an embodiment of the present invention to obtain the advantage of improved flexibility in all bending directions. The array core 300 has electrode wires 302 embedded within by an elongated planar thin film array core 301. At the end of each electrode wire 302 is a stimulation contact 303. At least a portion of the thin film array core 301 is formed into an elongated helical shape having helical turns that provides the desired improved flexibility. The helical shape of the stacked or folded thin film array core 301 can be realized, for example, by first shaping the core into the desired form by winding around a rod 304 with subsequent thermo-forming heat treatment to permanently fix the shape, or by shaping the core into the desired helical shape and then inserting it into a flexible tube for holding the shape.

FIG. 4 shows an example of helical shaped array core 300 which has been over-molded with a resilient electrode carrier 401 such as biocompatible silicone to form a whole electrode array 400. The silicone material of the electrode carrier 401 establishes a smooth outer surface over the array core 300 to further reduce insertion trauma. The molding of the electrode carrier 401 can be based on injection molding or by insertion of the thin film array core 301 into a silicone support tube. Surface openings in the electrode carrier 401 can be made over the stimulation contacts 303, for example, by masking the stimulation contacts 303 during to the molding process or by post-molding laser or mechanical treatment to selectively remove the silicone carrier material. The silicone electrode carrier 401 also adds some mechanical stability to the highly flexible shaped electrode array 400 to avoid compression and kinking during implantation into the cochlea.

In such an electrode array 400, the bend control elements may be formed by sections of the electrode carrier 401 between the helical turns of the array core 300. The helical structure of the array core 300 may have the desired property of easily bending in the lateral direction due to its helical design. However, the silicone material of the encasing electrode carrier 401 may actually act in the opposing way to resist lateral bending. So if the array core 300 has a high number of helical turns, then the array core 300 easily bends laterally; but at the same time, because there are many helical turns, there is less silicone carrier material between them. So the interstitial silicone material of the electrode carrier 401 between the helical turns of the electrode core 300 is stretched quite substantially and resists the bending force. On the other hand, if the number of helical turns is low, the array core 300 is less flexible and requires greater force to bend laterally, but there also is less resistive force of the silicone material of the electrode carrier 401 because the portion between the helical turns is larger.

While FIG. 3 shows an array core 300 having a number of helical turns and a number of stimulation contacts 303 that are equal, other specific embodiments may be different and it may be that not every helical turn contains a stimulation contact 303. For example, FIG. 5 shows a helical shaped array core 300 having a stimulation contact 303 on every other helical turn. FIG. 6 shows an example of helical shaped array core 300 wherein the spacing between helical turns decreases from one end 601 to the other 602. FIG. 7 shows an example of helical shaped array core 300 wherein the helix diameter decreases from one end to the other. And FIG. 8 shows an example of helical shaped array core 300 wherein the stimulation contacts 303 have a trapezoid shape.

In the foregoing embodiments, the stimulation contacts all are much wider than the electrode wires. FIG. 9 A-D shows an example of another embodiment of an array core 900 wherein the exposed ends of the electrode wires 902 themselves form the stimulation contacts 903. FIG. 9 A shows an electrode subassembly where multiple insulated electrode wires 902 are supported on a thin film array core 901. The terminal ends of the electrode wires 902 are uninsulated and exposed to form the stimulation contacts 903. As shown in FIG. 9 B, multiple electrode subassemblies are arranged in series to form a complete array core 900. The thin film array cores 901 are then thermoformed into a helical shape as shown in FIG. 9 C, and enclosed in resilient electrode carrier material 904 as shown in FIG. 9 D which leaves exposed only the long thin wire ends of the stimulation contacts 903. In specific embodiments, these wire end stimulation contacts 903 may extend over one or more helical turns.

Given the small cross-sectional size of potential insertion sites such as the scala tympani of the cochlea, the curvature of the helical turns must be great enough to allow the electrode array to fit in the desired location without damaging the delicate tissue structures involved. This means that the electrode wires and the stimulation contacts must be significantly deformed from their original planar shape as found in the original subassembly. For large structures such as the stimulation contacts, this bending may be difficult to achieve without damaging the polymer film core and/or the material (such as platinum) of the contact itself.

One solution to this problem is to divide each stimulation contact into two or more smaller sections in the direction of the helical bending with one or more thinner connecting sections that electrically connect the contact sections. Bending will then preferentially occur at these thinner connecting sections and less or not at all in the larger and more rigid contact sections. FIG. 10 A-D shows an example of helical shaped array core 1000 wherein each stimulation contact 1003 is split into contact sections 1004 with one or more connecting sections 1005. In the example shown in FIG. 10, each stimulation contact 1003 is divided into two semi-circular contact sections 1004 with narrow connecting section 1005 at either end. When initially fabricated into an electrode subassembly on a thin film array core 1001 as shown in FIG. 10 C, the stimulation contacts 1003 remain in the planar form of the core. During the electrode shaping process when a group of array core subassemblies is wound into helical form as shown in FIG. 10 D, the connecting sections 1005 bend easily as shown in detail in FIG. 10 B to accommodate the helical shape.

The foregoing examples have a relatively constant amount of flexibility from one end of the electrode array to the other, but that is not necessarily always the case. For example, it is generally desirable that the basal end of the electrode array be stiffer (more rigid) and less flexible than the apical end to improve the surgical handling and avoid kinks or collapses in the electrode during surgical insertion. In addition, the base end should be stiff enough to overcome the frictional forces between the electrode array and the target tissue without kinking. One way to achieve this is by using more layers of the core material towards the base end than the apical end.

Figure 1:
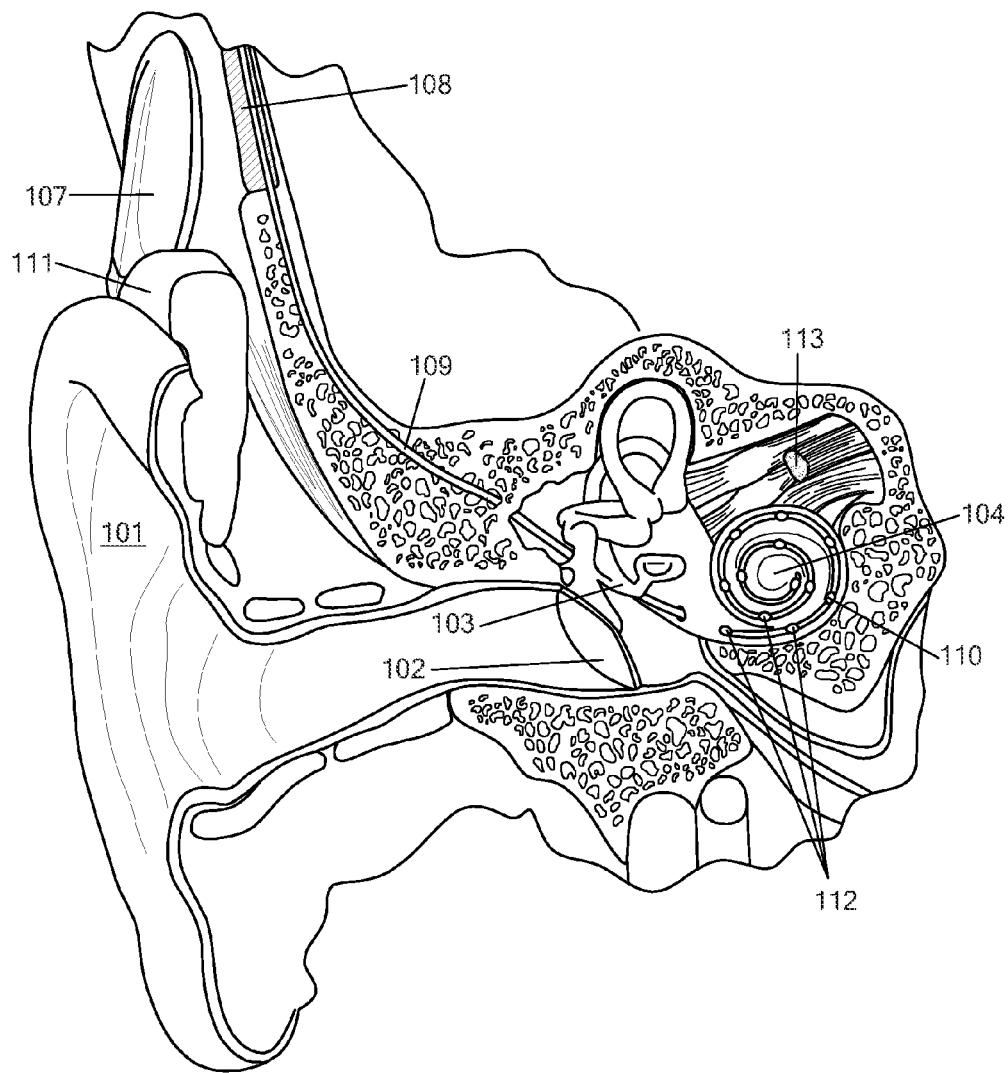
FIG. 1 shows anatomical structures in a human ear having a cochlear implant system.
Figure 9A:
FIG. 9 A-D shows an example of helical shaped array core wherein the exposed ends of the electrode wires form the stimulation contacts.
Figure 9B:
Figure 9C:
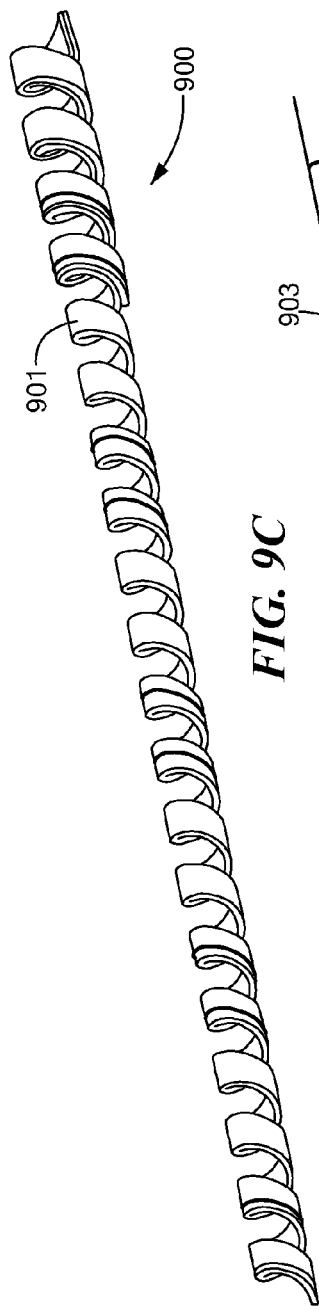
Figure 9D:
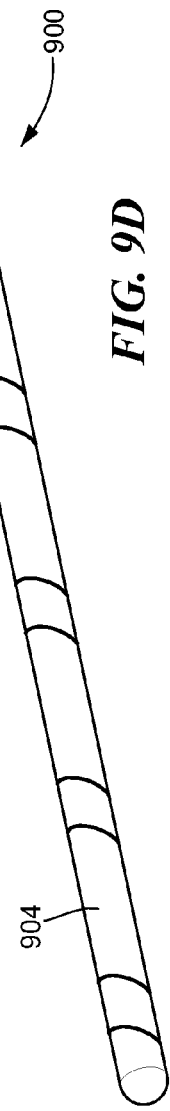
Figure 10A:
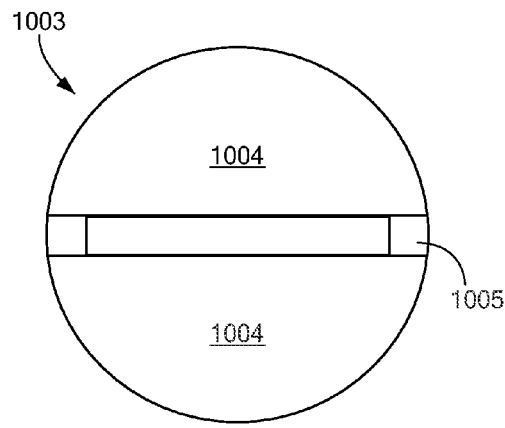
FIG. 10 A-D shows an example of helical shaped array core wherein each stimulation contact is split into contact sections with connecting sections.
Figure 10B:
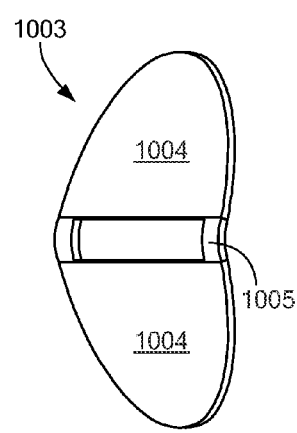
Figure 10C:
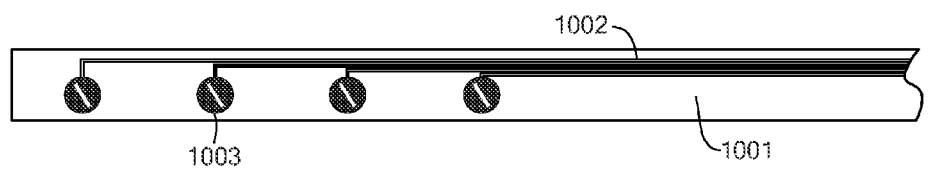
Figure 10D:
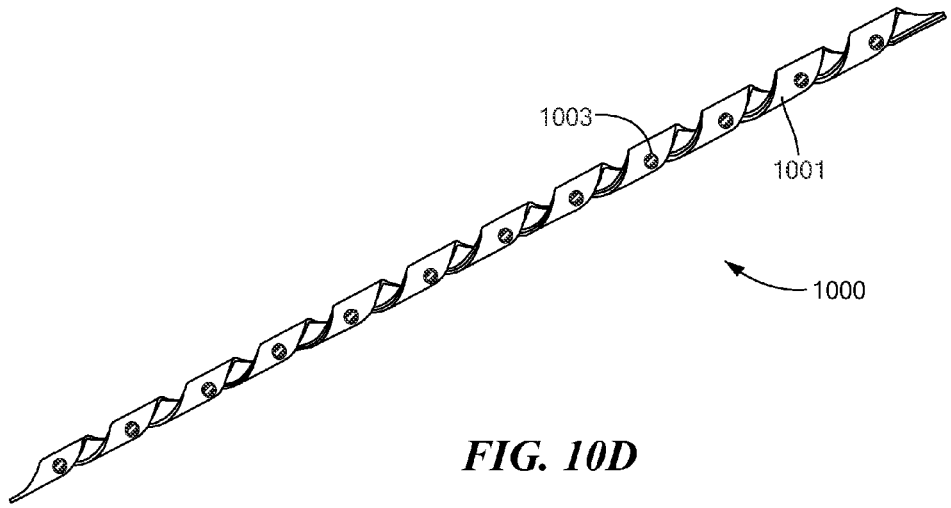
Figure 11A:
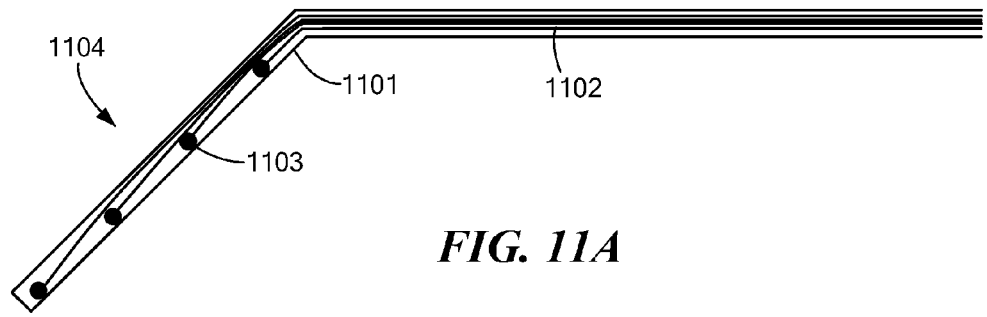
FIG. 11 A-C shows an example of helical shaped array core wherein each array core divides into an angled branch.
Figure 11B:
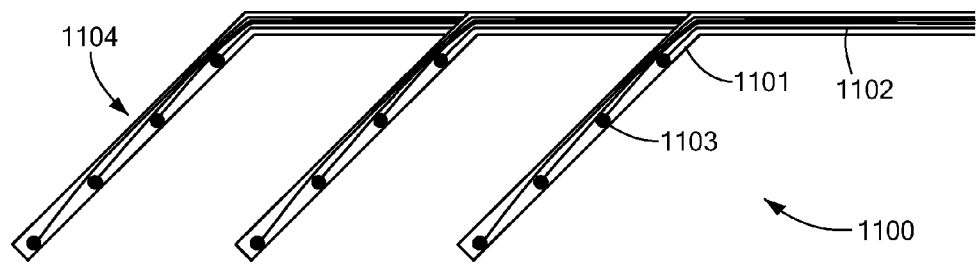
Figure 11C:
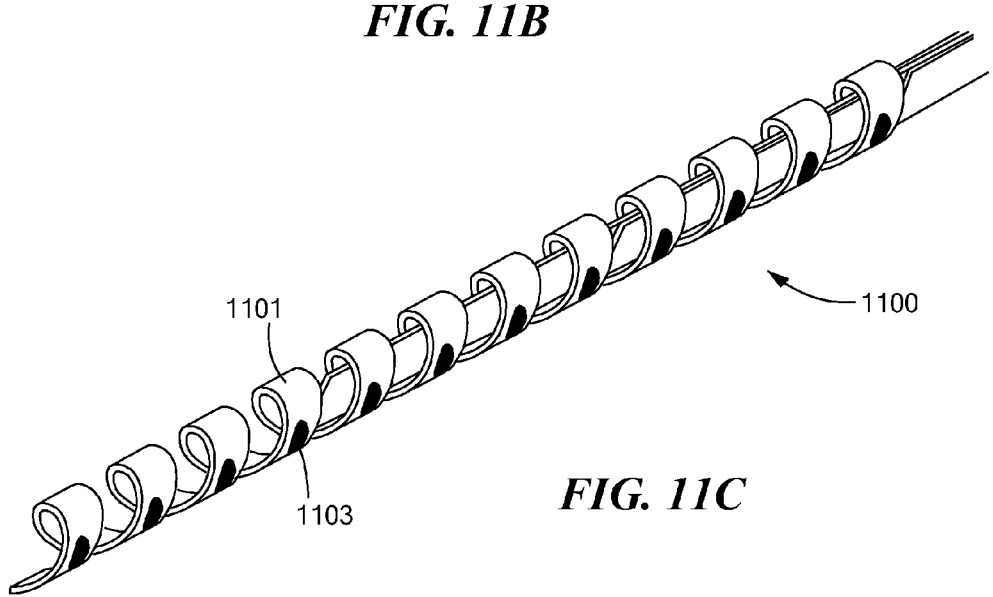

FIG. 11 A-C shows an example of such an array core 1100 based on an electrode array core 1101 that divides into angled branches 1104. FIG. 11 A shows a single array core subassembly wherein the thin film array core 1101 has an angled branch 1104. In FIG. 11 B, three branched array subassemblies are stacked together to form a complete planar form array core 1100. The individual angled branches 1104 can then be helically wound around the straight segments of the array core 1101 which has three layers near the base end, progressively decreasing to two, then one, then no layers towards the apical end of the array core 1100. This layered progression of the straight segments of the core 1101 changes the flexibility of the array core 1100 from relatively rigid near the base end (and consequently easier for the surgeon to manipulate) to maximally flexible at the apical end (minimizing tissue trauma).

The foregoing embodiments describe highly flexible electrode arrays which are all based on a helical shaped thin film array core. However a thin film array core can be formed into other shapes that also provide improved flexibility. For example, FIG. 12 shows an example of an array core 1200 having a thin film array core 1201 formed into a wavy shape having a plurality of recurring waves according to an embodiment of the present invention. U.S. Pat. No. 6,843,870 previously proposed such a wave shape for an implantable cable structure, but this shape has not previously been considered or adapted for an array core for insertion into delicate tissues such as cochlear structures. In the embodiment shown in FIG. 12, the array core 1200 is arranged to have a stimulation contact 1203 positioned on the peak of each wave shape, but other embodiments may be arranged differently, for example, having a stimulation contact 1203 on every other wave or having one portion of the array core 1200 where there are stimulation contacts 1203 on every wave and another portion of the array core 1200 where there are stimulation contacts 1203 on every second wave, etc.

FIG. 13 shows an example of molding arrangement for manufacturing a wavy shape thin film array core 1200 according to an embodiment of the present invention. A planar form of the electrode 1200 in which the core 1201 is made of a thermoformable polymer material is placed in heat treatment mold having complementary wave shaped blocks 1301 and 1302. As the mold blocks 1301 and 1302 are heated, the array core 1201 softens and conforms to the wave shapes of the molds, in which form it then hardens after cooling.

In some embodiments, it may be advantageous to have sections which are shaped differently. For example, FIG. 14 shows an example of a thin film array core 1400 having a helical shape section 1402 towards the apical end for increased flexibility, and a planar section 1401 at the base end which is more rigid and therefore easier for the surgeon to handle.

Figure 21:
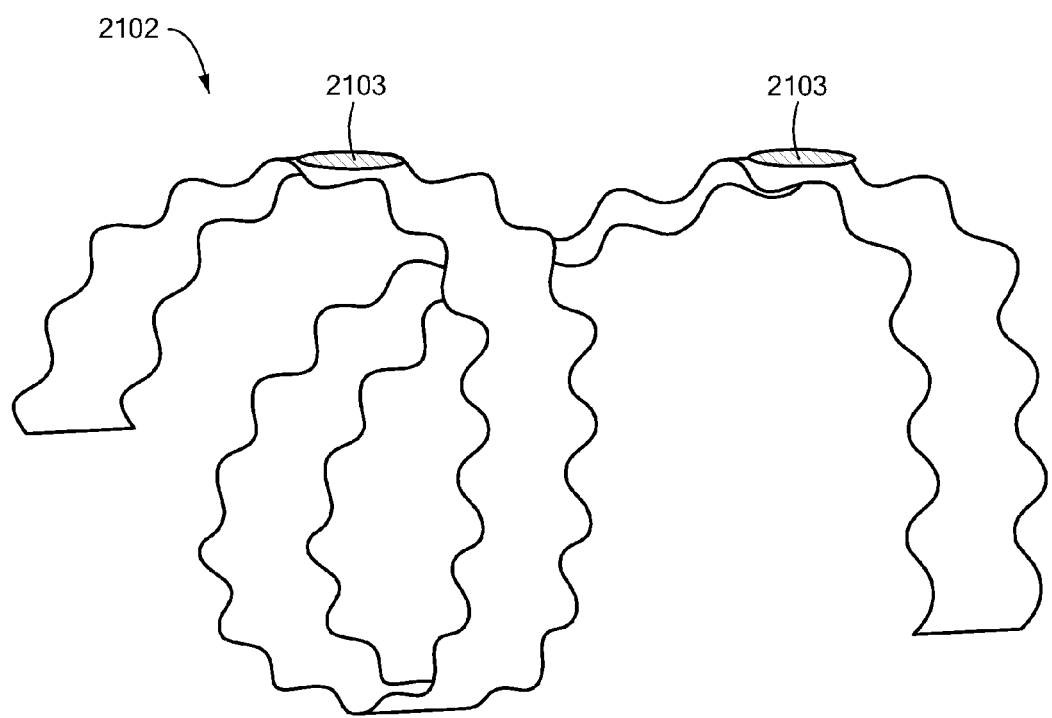
FIG. 21 shows an example of a thin film array core related to the one shown in FIG. 14 having a helical wound portion with a smaller recurring waveform pattern within the core material.

FIG. 21 shows an example of a thin film array core related to the one shown in FIG. 14 having a helical wound portion 2102 with a smaller recurring waveform pattern within the thin film material. Such a mixed pattern of a smaller recurring waveform within a larger helical winding can be shaped by initially stacking the thin film core and heating to some first temperature T1 that softens the thin film and allows it to be shaped into a wave-shape form, and then cooled to maintain the wave-shape. The thin film core can then be heated again to a different temperature T2 (somewhat lower than T1), shaped into the elongated helix form, and then cooled to retain the helix shape with the smaller recurring wave-form.

FIG. 15 shows another similar example of a thin film array core 1500 having a wavy shape section 1502 and a planar section 1501. The embodiments shown in FIGS. 14 and 15 have stimulation contacts 1403 and 1503 respectively on both sections of the array core, which is not necessarily the case in other embodiments, which may have stimulation contacts in just one section, or even just a portion of one section.

Figure 16A:
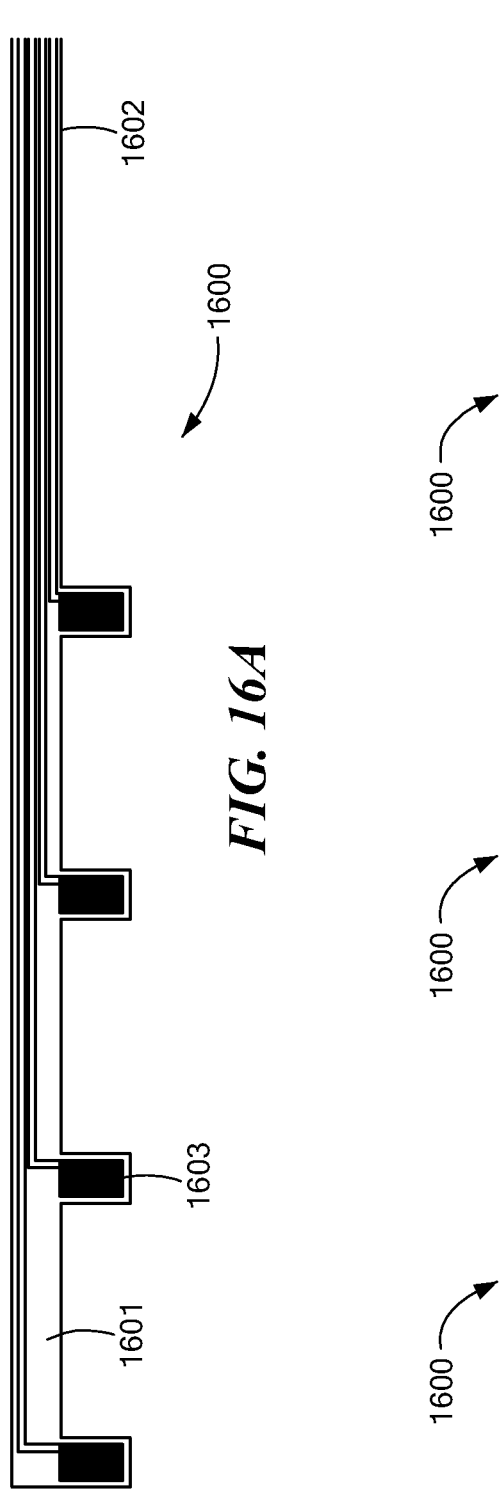
FIG. 16 A-B shows an example of a thin film implant array core having contact wings for stimulation contacts.
Figure 16B:
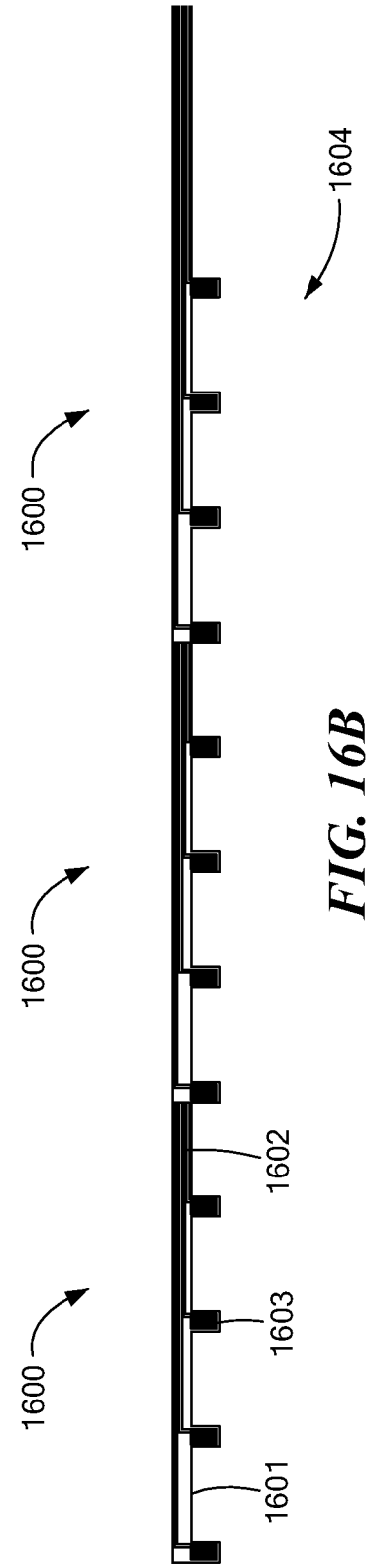
Figure 17:
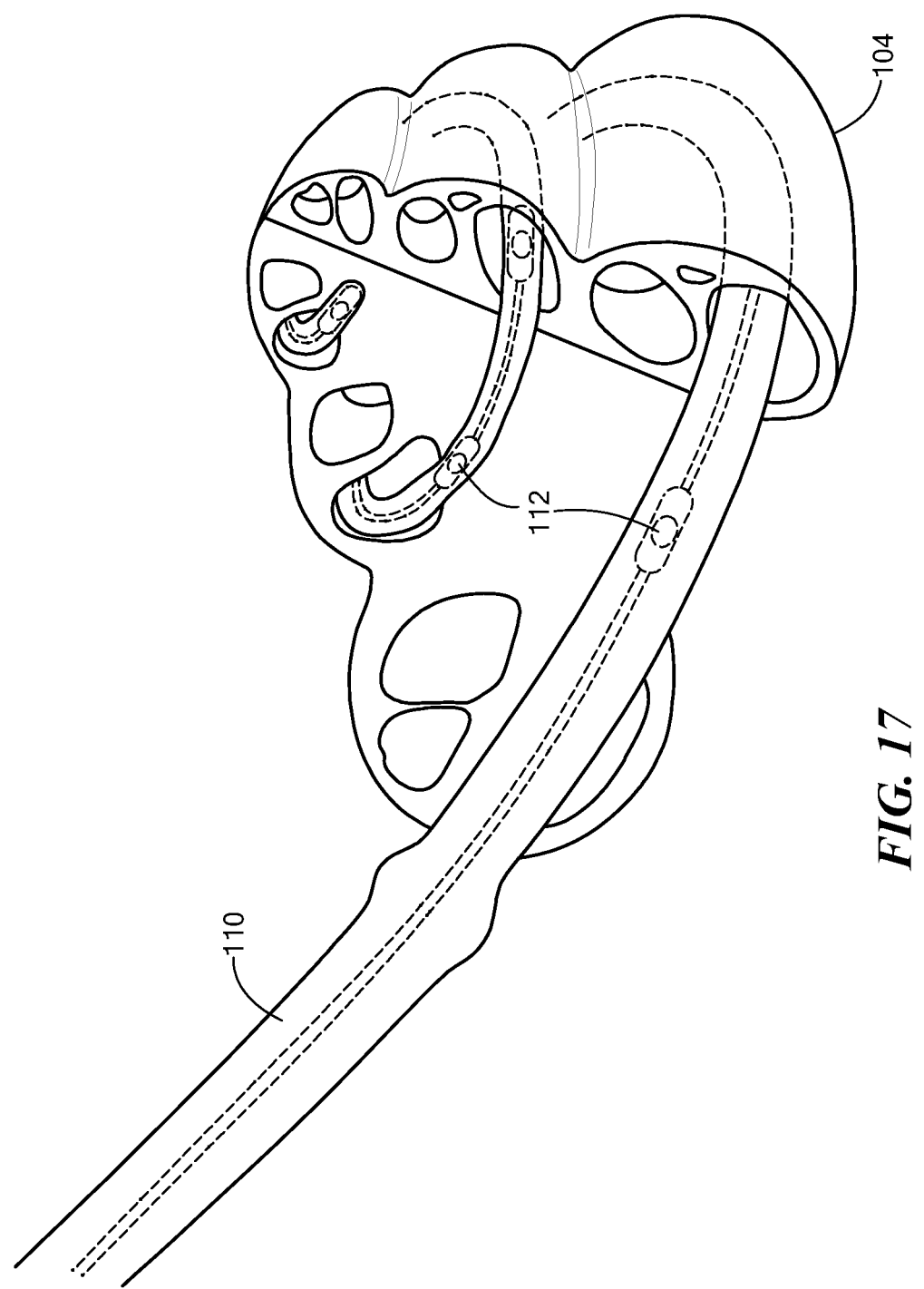
FIG. 17 shows an elevated perspective cross-sectional view of a cochlea containing an electrode array.

The stimulation contacts need to have some minimum area for safe electro-stimulation. In order to reduce the amount (width) of the thin film array core as much as possible (and thereby further increase the flexibility), it may be useful to keep the wire portion of the supporting core as narrow as possible and only increase the assembly width with protrusions at the stimulation contacts. FIG. 16 A-B shows an example of another form of a thin film array core based on using contact wings for stimulation contacts. FIG. 16A shows an electrode subassembly 1600 having multiple electrode wires 1602 supported by a thin film array core 1601 which includes lateral protrusions that support the contact wing stimulation contacts 1603. FIG. 16 B shows an entire array core 1604 formed of multiple layered subassemblies 1600. Such an arrangement of contact wings minimizes the amount of polymer film core 1601 used, thereby increasing flexibility of the resulting array core 1604. Such an array core may be used in the various ways and forms previously described.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable electrode array comprising:
    a plurality of electrode wires for carrying electrical stimulation signals;
    at a terminal end of each electrode wire, an electrode stimulation contact for applying the electrical stimulation signals to adjacent neural tissue;
    an electrode carrier of resilient material encasing the electrode wires and having an outer surface with a plurality of contact openings exposing the stimulation contacts;
    an electrode array core encased within the electrode carrier, the array core being made of a flexible polymer material within which are embedded the electrode wires and the array core including;
    i. an elongated planar portion, and
    ii. an elongated helical portion having a plurality of helical turns; and
    a plurality of bend control elements distributed along the length of the electrode array to control bending flexibility of the electrode array as a function of a bend radius threshold.

2. An implantable electrode array according to claim 1, wherein the bend control elements are made of a softer material than the electrode carrier material.

3. An implantable electrode array according to claim 1, wherein the bending flexibility is adapted to be greater for bending less than the bend radius threshold and lesser for bending greater than the bend radius threshold.

4. An implantable electrode array according to claim 1, wherein the bending flexibility is anisotropic to be greater in one direction than another.

5. An implantable electrode array according to claim 1, wherein the bend control elements are distributed along the length of the electrode array between helical turns of the array core.

6. An implantable electrode array according to claim 1, wherein the elongated helical portion contains a plurality of recurring waves within each helical turn of the array core.

7. An implantable electrode array according to claim 1, wherein every helical turn has a stimulation contact.

8. An implantable electrode array according to claim 1, wherein not every helical turn has a stimulation contact.

9. An implantable electrode array according to claim 8, wherein every second helical turn has a stimulation contact.

10. An implantable electrode array according to claim 1, wherein the array core has a constant distance between helical turns.

11. An implantable electrode array according to claim 1, wherein the array core has a variable distance between helical turns.

12. An implantable electrode array according to claim 1, wherein the helical shape has a substantially constant diameter.

13. An implantable electrode array according to claim 1, wherein the helical shape has a diameter that decreases towards one end.

14. An implantable electrode array according to claim 1, wherein the array core is substantially hollow.

15. An implantable electrode array according to claim 1, wherein the array core contains a core material polymer that is harder than the carrier material.

16. An implantable electrode array according to claim 1, wherein each stimulation contact includes a plurality of electrically connected split contact sections.

17. An implantable electrode array according to claim 1, further comprising a plurality of contact wings perpendicular to the electrode wires and on which the stimulation contacts are distributed.

18. An implantable electrode array according to claim 17, wherein the contact wings are supported by the array core.

* * * * *